United States Patent [19]

Perrier et al.

[11] Patent Number: 5,202,126
[45] Date of Patent: Apr. 13, 1993

[54] COMPOSITION CONTAINING PREGNENOLONE OR A PREGNENOLONE ESTER INCORPORATED IN LIPOSOMES, AND A METHOD FOR REGENERATING, OR REVITALIZING THE SKIN THEREWITH

[75] Inventors: Pierre Perrier, Orleans; Gérard Redziniak, Saint Cyr en Val; Patrice Andre, Neuville Aux Bois, all of France

[73] Assignee: Parfums Christian Dior, Paris, France

[21] Appl. No.: 737,933

[22] Filed: Jul. 29, 1991

Related U.S. Application Data

[63] Continuation of Ser. No. 477,811, Feb. 16, 1990, filed as PCT/FR88/00412, Aug. 11, 1988, abandoned.

[30] Foreign Application Priority Data

Aug. 20, 1987 [FR] France ............... 87 11773

[51] Int. Cl.⁵ .................................... A61K 31/47
[52] U.S. Cl. .................................... 424/450; 424/401; 514/169; 514/171; 514/182; 514/844
[58] Field of Search ............... 424/450, 401; 514/844, 514/169, 171, 182

[56] References Cited

U.S. PATENT DOCUMENTS

| | | | |
|---|---|---|---|
| 2,791,534 | 5/1957 | Basel et al. ............... | 514/171 |
| 4,474,763 | 10/1984 | Lubowe ............... | 424/177 |
| 4,614,796 | 9/1986 | Kawamata et al. ............... | 536/5 |
| 4,780,455 | 10/1988 | Lieberman et al. ............... | 514/77 |
| 4,830,858 | 5/1989 | Payne et al. ............... | 424/450 |
| 4,895,727 | 1/1990 | Allen ............... | 424/642 |
| 4,906,477 | 3/1990 | Kurono et al. ............... | 424/450 |
| 4,996,098 | 2/1991 | Perusich et al. ............... | 428/229 |

FOREIGN PATENT DOCUMENTS 2344290 10/1977 France.

OTHER PUBLICATIONS

Deamer et al., 1983 In: liposomes, Ostro M. ed., Dekker, Inc., pp. 26-51.
Liposomes in topical drug delivery. Schaeffer et al. Invest. Opthalmol. Vis. Sci. p. 220, 1980.

Primary Examiner—Thurman K. Page
Assistant Examiner—G. S. Kishore
Attorney, Agent, or Firm—Bryan Cave

[57] ABSTRACT

The present invention relates to a composition based on hydrated lipidic lamellar phases or on liposomes.

In this composition, pregnenolone or a pregnenolone ester, such as, in particular, pregnenolone acetate, sulfate or palmitate, is at least partially incorporated in the said hydrated lipidic lamellar phases or the said liposomes.

This composition can be applied in particular in the cosmetic or pharmaceutical sector, especially the dermatological sector, for the preparation of compositions with regenerating or revitalizing activity.

13 Claims, 2 Drawing Sheets

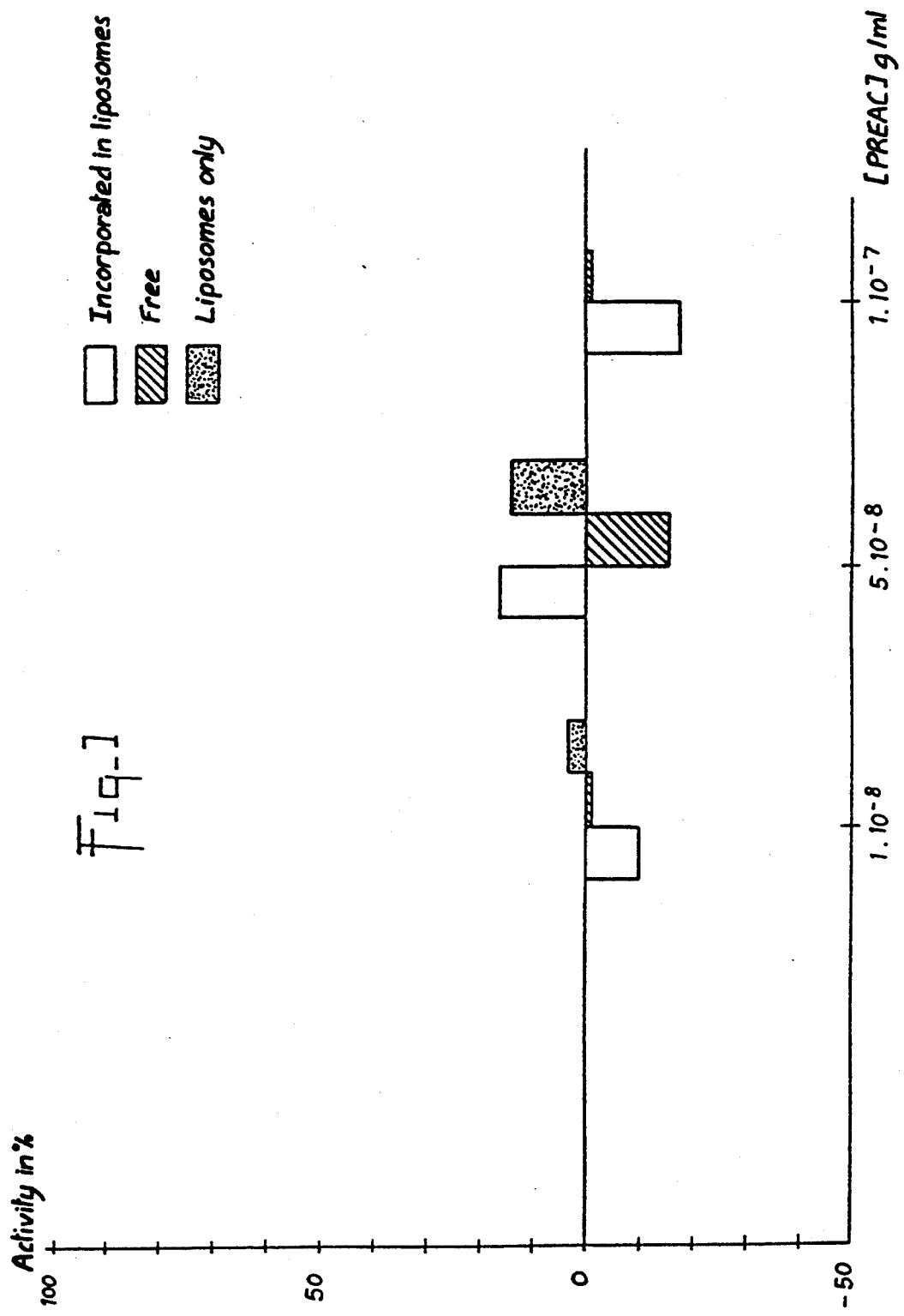

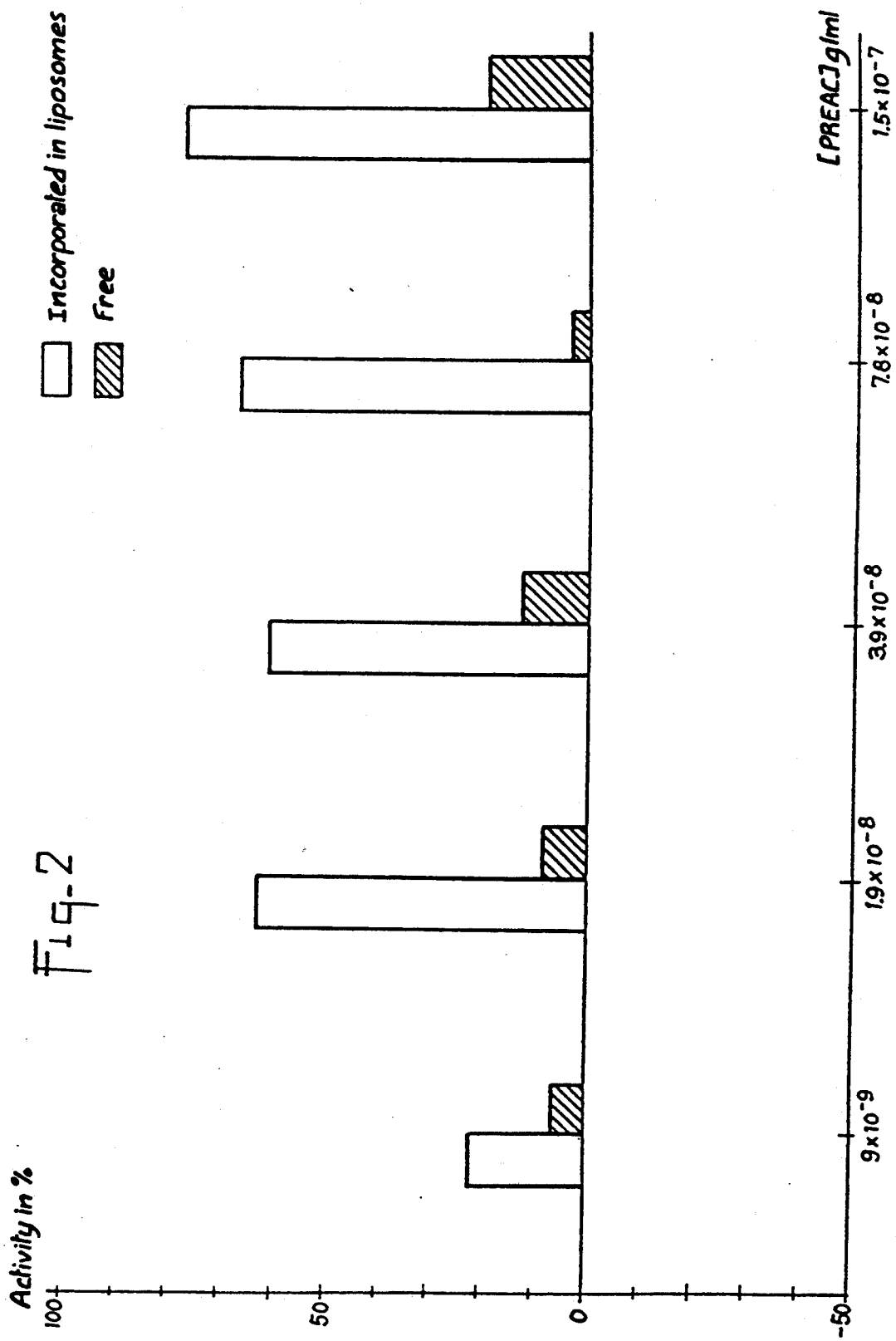

COMPOSITION CONTAINING PREGNENOLONE OR A PREGNENOLONE ESTER INCORPORATED IN LIPOSOMES, AND A METHOD FOR REGENERATING, OR REVITALIZING THE SKIN THEREWITH

This is a continuation of U.S. application Ser. No. 07/477,811, filed Feb. 16, 1990, filed as PCT/FR88/00412, Aug. 11, 1988, now abandoned which is incorporated by reference herein.

The present invention relates essentially to a composition based on hydrated lipidic lamellar phases or on liposomes containing pregnenolone or a pregnenolone ester.

The invention can be applied in particular in the cosmetic or pharmaceutical sector, especially the dermatological sector, for the preparation of compositions with regenerating or revitalizing activity.

Steroids have already been used for the preparation of pharmaceutical or cosmetic compositions for treating the skin. U.S. Pat. No. 2,791,534 and British patent 768 129, for example, disclose the use of steroids as agents with antiwrinkle activity.

The effect of hormones on the skin has been studied more particularly and it is indicated in the article published in J. Soc. Cosmetic Chemists, volume 18, pages 549 to 562 (Aug. 19, 1967) that testosterone produces a rejuvenating effect on the skin and that progesterone and pregnenolone, which are intermediates in the biosynthesis of testosterone, produce a similar effect, although to a much smaller extent, which is particularly weak in the case of pregnenolone.

It is for this reason that pregnenolone, either in the free form or in the form of an ester, has often been used, for treating the skin, in combination with other active agents.

Thus U.S. Pat. No. 4,474,763 describes an antiwrinkle composition containing pregnenolone and elastin, which is a skin protein known for its antiwrinkle activity.

Likewise U.S. Pat. No. 3,326,901 discloses a composition with an anti-irritating and antidehydrating action which contains pregnenolone and allantoin.

The antidehydrating effect of pregnenolone on the skin has also been mentioned more recently in French patent application no. 2 405 069. This patent application proposes a hormonal pharmaceutical composition containing a water-soluble estrogen (estrone), a liposoluble estrogen (estradiol), an androgen (testosterone) and, if appropriate, pregnenolone to give the composition an antidehydrating effect. According to the author of the said patent application, only the sex hormones, i.e. male hormones and female hormones, are capable of staving off the skin deterioration phenomena due to the combined action of age and climatic aggression; on the other hand, it is indicated that pregnenolone plays no part in the skin restoration processes.

Analysis of the prior art therefore shows that the use of pregnenolone or a pregnenolone ester alone, in skin treatment, has always been limited because of the very weak activity of this substance.

Furthermore, it is already known to use hydrated lipidic lamellar phases or liposomes in pharmaceutical compositions or cosmetic compositions incorporating a variety of active principles (U.S. Pat. No. 4,508,703).

It has now been discovered, totally surprisingly and unexpectedly, that pregnenolone or its esters have an enhanced regenerating and revitalizing activity on the skin and superficial body growths when this substance is at least partially incorporated in a hydrated lipidic lamellar phase or in liposomes. In particular, a quite remarkable improvement has been observed in the activity of pregnenolone on protein synthesis.

It is thus possible to deduce that the activity of pregnenolone or pregnenolone esters is subject to some kind of potentiating effect in hydrated lipidic lamellar phases or in liposomes.

Thus the effect of the present invention is to solve the new technical problem of providing a novel formulation of pregnenolone or a pregnenolone ester which makes it possible to potentiate their efficacy so as to enable them to be used in cosmetic or pharmaceutical compositions, especially dermatological compositions, with regenerating or revitalizing activity.

Thus, according to a first aspect, the present invention provides a composition based on a hydrated lipidic lamellar phases or on liposomes, wherein pregnenolone or a pregnenolone ester, preferably pregnenolone acetate, sulfate or palmitate, is at least partially incorporated in said hydrated lipidic lamellar phases or the said liposomes.

In another advantageous embodiment of the invention, a sterol, preferably $\beta$-sitosterol, is also at least partially incorporated in the above-mentioned hydrated lipidic lamellar phases or the liposomes of the above-mentioned composition.

More particularly, the sterol is incorporated in the lipidic phase of the hydrated lipidic lamellar phases or of the liposomes in a concentration by weight of between about 1% and 20%, preferably of about 10%.

In one modified embodiment of this composition, the pregnenolone or the pregnenolone ester of the said composition, by itself or mixed with the sterol, is introduced into the lipidic phase of the hydrated lipidic lamellar phases or of the liposomes.

More particularly, the concentration of pregnenolone or pregnenolone ester is between about 0.05% and 20%, preferably between about 1% and 15% and more preferably between about 1% and 5% of the weight of the said lipidic phase, so that the sum of the concentrations in this phase of pregnenolone or pregnenolone ester, on the one hand, and any sterol present, on the other, does not exceed about 25% and preferably about 20%.

In another modified embodiment of this composition, the pregnenolone ester of the said composition is introduced into the aqueous phase of the hydrated lipidic lamellar phases or of the liposomes. In this case, of course, the solubility of the said ester in water must be such that at least the desired concentration can be obtained in the said lamellar phases or the said liposomes.

More particularly, the concentration of the pregnenolone ester is between about 0.001% and 5% and preferably between about 0.01% and 2% of the weight of the said aqueous phase.

The incorporation of the pregnenolone or its esters, and if appropriate the sterol, into the hydrated lipidic lamellar phases or into the liposomes according to the invention can be carried out by known processes. These are chosen more particularly according to the degree of lipophilicity or hydrophilicity of the compound to be incorporated.

In a preferred embodiment of the composition based on hydrated lipidic lamellar phases or on liposomes according to the invention, a preparative technique described in U.S. Pat. No. 4,508,703, in combination, if appropriate, with a technique described in U.S. Pat. No. 4,621,023, is chosen.

According to a second aspect, the present invention further relates to a cosmetic or pharmaceutical composition, especially a dermatological composition, with regenerating or revitalizing activity, which comprises a composition based on hydrated lipidic lamellar phases or on liposomes, as defined previously.

The proportion by weight of the pregnenolone or the pregnenolone ester is preferably between about 0.0005% and 5%, more preferably between about 0.002% and 1% and most preferably between about 0.01 and 0.5% by weight, relative to the total weight of the composition.

Other objects, characteristics and advantages of the invention will become more clearly apparent from the following explanatory description referring to several illustrative Examples, which cannot in any way limit the scope of the invention. In these Examples, the percentages are given by weight, unless indicated otherwise.

BRIEF DESCRIPTION OF THE DRAWINGS

FIG. 1 is a histogram showing the effect of pregnenolone acetate on the number of human fibroblasts in culture.

FIG. 2 is a histogram showing the effect of pregnenolone acetate on the protein content of the fibroblasts.

EXAMPLE 1

A—Preparation of a Composition in the Form of a Lipidic Powder Containing Pregnenolone Acetate 100 mg of pregnenolone acetate and 1 g of β-sitosterol are dissolved in 100 ml of methylene chloride and 8.9 g of soya lecithin are added, if appropriate in the presence of a lipophilic antioxidant, for example 0.2 g of α-tocopherol.

The solution obtained is atomized at 65° C. in the manner described in U.S. Pat. No. 4,508,703. This gives a lipidic powder composed of small, substantially spherical particles with a diameter of about 1 to 40 nm.

B—Preparation of a Composition in the Form of a Liposome Suspension which is Advantageously Homogenized 5 g of the powder obtained in step A are dispersed in the appropriate amount of water to give a final volume of 250 ml. This operation is carried out at ordinary temperature for 1 h, with magnetic stirring.

This gives a liposome suspension after homogenization either by means of ultrasound or by means of a homogenizer under pressure, for example according to the process described in U.S. Pat. No. 4,621,023.

If, for example, homogenization is effected by treatment with ultrasound for 15 min, liposomes with a size of between 135 and 186 nm are obtained.

250 ml of a homogenized liposome suspension in which the proportion of lipidic phase is 2% are therefore obtained after this step B.

EXAMPLES 2 TO 7

Compositions in the Form of Liposome Suspension Containing Pregnenolone Acetate

Several compositions in the form of liposome suspensions are prepared by the process described in Example 1, the proportions of the constituents of the lipidic phase being varied.

Table I below indicates the compositions of the different suspensions obtained.

EXAMPLES 8 TO 10

Compositions in the Form of Liposome Suspensions Containing Pregnenolone

Different liposome compositions are prepared by the process of Example 1, the pregnenolone acetate being replaced with pregnenolone and the proportions of the constituents of the lipidic phase being varied. The compositions of the different liposome suspensions are shown in Table I.

TABLE I

| Example no. | | 1 | 2 | 3 | 4 | 5 | 6 | 7 | 8 | 9 | 10 |
|---|---|---|---|---|---|---|---|---|---|---|---|
| Composition | soya lecithin | 89 | 80 | 85 | 80 | 75 | 70 | 90 | 89 | 80 | 80 |
| of the | β-sitosterol | 10 | 10 | 10 | 10 | 15 | 20 | 0 | 10 | 10 | 10 |
| lipidic | pregnenolone | 1 | 10 | 5 | 10 | 10 | 10 | 10 | 0 | 0 | 0 |
| powder, | acetate | | | | | | | | | | |
| % by weight | pregnenolone | 0 | 0 | 0 | 0 | 0 | 0 | 0 | 1 | 10 | 10 |
| Concentra- | lipidic phase | 2 | 20 | 2 | 2 | 2 | 2 | 2 | 2 | 10 | 30 |
| tions in | pregnenolone | 0.02 | 2 | 0.1 | 0.2 | 0.2 | 0.2 | 0.2 | 0 | 0 | 0 |
| the liposome | acetate | | | | | | | | | | |
| suspension, | pregnenolone | 0 | 0 | 0 | 0 | 0 | 0 | 0 | 0.02 | 1 | 3 |
| % by weight | | | | | | | | | | | |

EXAMPLE 11

Study of the Influence of the Sterol on the Stability of the Liposomes Containing Pregnenolone or a Pregnenolone Ester The aim is to determine the influence of β-sitosterol on the stability of the liposomes according to the invention.

This is done by preparing a reference suspension according to the process of Example 1, the composition of the lipidic phase being 90% of soya lecithin and 10% of β-sitosterol.

The stability of the liposomes is evaluated by determination of their size using an appropriate instrument such as a NANOSIZER ®. Measurements are taken at time zero (when preparation is complete) at room temperature and then on day 8 and day 15 at 4° C., room temperature and 40° C. The polydispersity, which quantifies the scatter of the liposome sizes, and the mean size, are shown in Table II for each measurement. The quality of the liposome suspension, one of the criteria of which is the stability, is generally better the smaller the values of these quantities and the more uniform they are with time.

The stability of the liposomes can therefore be evaluated by measuring their size since it is known that, if they are unstable, the liposomes tend to fuse together, they increase in size and, beyond a certain size, they form a sediment.

Table II clearly shows that the incorporation of pregnenolone acetate is favored by the presence of β-sitosterol. When the powder contains no β-sitosterol (Ex. no. 7), sedimentation is observed after 8 d at 40° C. and the values of the polydispersity and size are large.

In the other cases, the size of the liposomes remains substantially constant and at an acceptable value.

Moreover, Table II shows that the incorporation of β-sitosterol in a proportion of more than about 15% by weight (Ex. no. 6) in the lipidic powder causes sedimentation phenomena and detracts from the stability of the liposomes containing pregnenolone acetate.

The advantage of the presence of β-sitosterol is clearly apparent, its concentration preferably being 10% of the weight of the lipidic phase (Ex. no. 4).

TABLE II

| Example no. | | | 3 | 4 | 5 | 6 | 7 | Reference |
|---|---|---|---|---|---|---|---|---|
| Composition of the lipidic powder, % by weight | lecithin | | 85 | 80 | 75 | 70 | 90 | 90 |
| | β-sitosterol | | 10 | 10 | 15 | 20 | 0 | 10 |
| | pregnenolone acetate | | 5 | 10 | 10 | 10 | 10 | 0 |
| Size of the liposomes (polydispersity/size (nm)) | t = 0 | RT | 6/272 | 6/260 | 4/268 | 3/284 | 9/1200 | 3/140 |
| | t = 8 d | 4° C. | 5/247 | 5/252 | 4/294 | 4/290 | 9/1040 | 5/134 |
| | | RT | 7/386 | 5/253 | 5/292 | 4/300 | 9/1560 | 3/152 |
| | | 40° C. | 5/233 | 4/242 | 3/300 | 4/305 + sedimentation | sedimentation | 3/178 |
| | t = 15 d | 4° C. | | 7/420 | 4/299 | 4/310 | | |
| | | RT | | 6/300 | 4/320 | 4/294 + sedimentation | | |
| | | 40° C. | | 4/275 + sedimentation | 4/277 + sedimentation | 4/353 + sedimentation | | | t = time in days
RT = room temperature (about 20° C.)

EXAMPLE 12

Evaluation of the Multiplying Power of the Compositions According to the Invention on Human Fibroblasts in Culture The method of evaluating the multiplying power of substances on cells in culture is derived from the method of Mrs. ADOLPHE et al., J. Cosmetic Sci. (1983), 6, 55.

Human fibroblasts are cultivated in a Petri dish (35 mm) in MEM (Eagle's minimum essential medium) containing 5% of calf serum.

After 24 h (37° C., 5% $CO_2$), the medium is replaced with a mixture consisting of MEM and the test substance at different concentrations. This mixture has a calf serum concentration of 2.5%. A reference containing 2.5% of calf serum but no additional substances is prepared in parallel.

The cells are then incubated at 37° C. for 7 d in a humid atmosphere containing 5% of $CO_2$. Three experiments are carried out for each culture.

After washing with phosphate buffer and detachment of the cells with trypsin, the cells are counted using an appropriate instrument.

The multiplying power of the substances is expressed by the following formula:

$$A.P. = \frac{N.P. - N\,2.5}{N\,2.5} \times 100$$

in which A.P. represents the multiplying power of the cells, N.P. represents the number of cells cultivated in the presence of the test substance and N 2.5 represents the number of cells cultivated in the reference, i.e. in the presence of 2.5% of calf serum.

The results obtained for different concentrations of pregnenolone acetate, abbreviated to PREAC, are represented in FIG. 1 in the form of a histogram.

FIG. 1 shows that, either free or incorporated in liposomes, the pregnenolone acetate has no significant effect on the increase in the number of human fibroblasts in culture.

EXAMPLE 13

Evaluation of the Stimulating Activity on Protein Synthesis

The activity on the protein content is evaluated by a method derived from the one described by JOHNSON and J. A. LOTT (1978), Clin. Chem. 24.

When the culture performed in Example 12 above is complete, the dishes are washed twice with phosphate buffer and then treated with 1 ml of sodium hydroxide solution (0.5N).

After shaking, 30 μl of cellular supernatant are added to 2 ml of a solution of Coomassie blue.

The protein concentration is obtained by measurement on a proti-analyzer (Marius Instruments), which automatically evaluates the ratio of the optical densities:

$$\frac{OD\ 590\ nm}{OD\ 465\ nm}$$

The activity on the "protein content" for each substance at each concentration is expressed by the formula:

$$T.P. = \frac{Ts - T_{2.5}}{T_{2.5}} \times 100$$

in which T.P. represents the activity on the protein content, Ts represents the protein content obtained on cultures in the presence of the test product and T2.5 represents the protein content obtained on cultures in the presence of the reference, i.e. in the presence of 2.5% of calf serum.

FIG. 2 shows the histogram of the results for the activity on the protein content at different pregnenolone acetate concentrations.

FIG. 2 very clearly demonstrates the stimulating action on protein synthesis of pregnenolone acetate incorporated in liposomes, whereas, in the free state, this same product exhibits practically no action.

In conclusion, the tests performed on cultures of human fibroblasts show the value of the compositions according to the invention in maintaining or restoring the normal biological processes of the skin and superficial body growths through their stimulating action on the synthesis of tissue proteins.

On the one hand, it is a known fact that this synthesis is slowed down when the cells divide. The absence of a particular action of the compositions according to the invention on cell division does not therefore constitute a handicap. On the other hand, the existence of tissue proteins is known to be important, in both quantity and quality, for the good physiological condition of the skin. The stimulating action of the compositions according to the invention on the synthesis of such proteins is therefore of very great interest, especially in cosmetics and in dermatology.

EXAMPLE 14

Gelled Composition Based on Liposomes

| soya lecithin | 0.89 g |
| --- | --- |
| β-sitosterol | 0.10 g |
| pregnenolone acetate | 0.01 g |
| gelled excipient qs | 100 g |

First of all a lipidic powder is prepared according to Example 1-A. This powder is then dispersed in water at a concentration of 4% according to Example 1-B and, if necessary, stabilized by means of a cosmetically or pharmaceutically acceptable preservative at the usual concentration.

The suspension obtained is then gelled by mixing 1 part of suspension with 3 parts of an aqueous gel of Carbopol ® 940 separately prepared in conventional manner at a concentration of 5%.

The gelled composition obtained can be used either for incorporation in cosmetic or pharmaceutical compositions, or as such, with added fragrances if desired, to care for the skin on the body or face, advantageously by daily application.

EXAMPLE 15

Cosmetic Composition in the Form of a Cream

| soya lecithin | 4 g |
| --- | --- |
| β-sitosterol | 0.5 g |
| Pregnenolone acetate | 0.5 g |
| excipient for oil-in-water emulsion qs | 100 g |

A suspension of liposomes according to Example 2, on the one hand, and an oil-in-water emulsion, on the other, are prepared separately. These two preparations are then mixed in proportions of 1 volume of liposome suspension to 3 volumes of emulsion.

The cream obtained is applied to the face, preferably in the evening.

EXAMPLE 16

Cicatrizant Dermatological Composition

| soya lecithin | 8 g |
| --- | --- |
| β-sitosterol | 1 g |
| pregnenolone acetate | 1 g |
| gelled excipients qs | 100 g |

This composition is obtained from the powder prepared according to Example 4 and dispersed at a concentration of 20% by means of a homogenizer under pressure. The dispersion obtained is then mixed with 1 volume equivalent of a 5% gel of Carbopol ® 940.

This composition has excellent cicatrizant properties. It is indicated in particular for the prevention and treatment of vergeture by application twice daily.

What is claimed is:

1. A composition comprising liposomes containing pregnenolone or a pregnenolone ester in the lipidic phase in an amount of between about 0.05 and 20% by weight of the lipidic phase.

2. The composition of claim 1, wherein the lipidic phase further comprises β-sitosterol.

3. The composition of claim 2, wherein the β-sitosterol is present in an amount of between about 1 and 20% by weight of the lipidic phase, and the sum of the concentrations of the pregnenolone or pregnenolone ester and the β-sitosterol in the lipidic phase does not exceed 25% by weight of the lipidic phase.

4. The composition of claim 1, wherein the concentration of the pregnenolone or pregnenolone ester is between about 0.0005 and 5% by weight of the composition.

5. The composition of claim 1, wherein the pregnenolone ester is selected from the group consisting of pregnenolone acetate, pregnenolone sulfate and pregnenolone palmitate.

6. The composition of claim 1, wherein the concentration of the pregnenolone or pregnenolone ester is between about 0.002 and 1% by weight of the composition.

7. The composition of claim 1, wherein the concentration of the pregnenolone or pregnenolone ester is between about 0.01 to 0.5% by weight of the composition.

8. A method for regenerating or revitalizing the skin by promoting tissue protein synthesis, which comprises applying to the skin a composition comprising liposomes containing pregnenolone or a pregnenolone ester in the lipidic phase in an amount of between about 0.05 and 20% by weight of the lipidic phase.

9. The method of claim 8, wherein said lipidic phase further comprises β-sitosterol.

10. The method of claim 9, wherein said β-sitosterol is present in an amount of between about 1 and 20% by weight of the lipidic phase, and the sum of the concentrations of the pregnenolone or pregnenolone ester and the β-sitosterol in the lipidic phase does not exceed 25% by weight of the lipidic phase.

11. The method of claim 8, wherein the pregnenolone ester is selected from the group consisting of pregnenolone acetate, pregnenolone sulfate and pregnenolone palmitate.

12. The method of claim 8, wherein the concentration of pregnenolone or pregnenolone ester is between about 0.002 and 1% by weight of the composition.

13. The composition of claim 8 wherein the concentration of pregnenolone or pregnenolone ester is between about 0.01 and 0.5% by weight of the composition.

* * * * *